United States Patent [19]

Murphree et al.

[11] Patent Number: 5,399,753
[45] Date of Patent: Mar. 21, 1995

[54] CATALYST RECOVERY IN THE CARBONYLATION OF CHLOROBUTENES TO PENTENOYL CHLORIDE

[75] Inventors: Bruce E. Murphree, Beaumont, Tex.; Emilio E. Bunel, Wilmington, Del.

[73] Assignee: DSM, N. V., Geleen, Netherlands

[21] Appl. No.: 237,983

[22] Filed: May 4, 1994

[51] Int. Cl.⁶ .................... C07C 51/58; C07C 53/00
[52] U.S. Cl. ............................................. 562/848
[58] Field of Search ........................................ 562/848

[56] References Cited

U.S. PATENT DOCUMENTS

| | | | |
|---|---|---|---|
| 2,627,360 | 5/1972 | Olivier | 562/848 |
| 3,309,403 | 3/1967 | Mador et al. | 562/848 |
| 3,338,961 | 8/1967 | Closson et al. | 562/848 |
| 3,423,456 | 1/1969 | Mador et al. | 562/848 |
| 3,536,739 | 10/1970 | Scheben et al. | 562/848 |
| 3,626,005 | 12/1971 | Scheben et al. | 562/848 |
| 3,627,827 | 12/1971 | Scheben et al. | 562/848 |
| 3,691,043 | 9/1972 | Thaler | 562/848 |
| 4,414,160 | 11/1983 | Erpénbach et al. | 562/848 |
| 4,749,525 | 1/1988 | Pascoe et al. | 562/848 |

FOREIGN PATENT DOCUMENTS

| | | |
|---|---|---|
| 40/22174 | 1/1965 | Japan . |
| 987274 | 3/1965 | United Kingdom . |

*Primary Examiner*—Paul J. Killos

[57] ABSTRACT

Palladium catalyst residue is recovered from still heels by treating the still heels with hydrochloric acid, converting the palladium component to crotyl palladium chloride, and using the crotyl palladium chloride as catalyst in the carbonylation of chlorobutene to 3-pentenoyl chloride.

3 Claims, No Drawings

CATALYST RECOVERY IN THE CARBONYLATION OF CHLOROBUTENES TO PENTENOYL CHLORIDE

FIELD OF THE INVENTION

This invention relates to the recovery and recycle of palladium catalyst in the process for the preparation of pentenoyl chloride by carbonylation of chlorobutenes.

BACKGROUND OF THE INVENTION

Bunel et al U.S. Pat. No. 5,288,903 discloses the preparation of pentenoyl chloride by the carbonylation of chlorobutenes using a palladium catalyst. In Example 1 the product mixture is distilled and the catalyst contained in the heel can be recycled to the carbonylation step.

SUMMARY OF THE INVENTION

The present invention is a process for the preparation of 3-pentenoyl chloride which comprises (a) treating the still heels obtained by the distillation of 3-pentenoyl chloride from a reaction mixture containing palladium catalyst residue with concentrated hydrochloric acid at a temperature in the range of 100 to 120 degrees C., (b) combining the product of step a with chlorobutene, (c) allowing the product of step b to form two phases, i.e. an organic phase, and a hydrochloric acid phase containing palladium catalyst residue, (d) separating the two phases of step c, (e) combining the hydrochloric acid phase obtained in step d with chlorobutene (f) distilling under a carbon monoxide atmosphere at a temperature of about 70 to 75 degrees C. the product of step e, an azeotropic mixture, until only one phase is observed, namely a phase containing chlorobutene and simultaneously formed crotyl palladium chloride, (g) heating the product of step f containing chlorobutene and crotyl palladium chloride at a temperature in the range of about 90 to 190 degrees C. under a carbon monoxide pressure of about 250 to 5,000 pounds per square inch, and (h) recovering 3-pentenoyl chloride from the product of step g by distillation. Still heels remain after step (h), and the still heels may be recycled to step (a). Preferably between steps f and g, the product of step f is dryed.

DETAILED DESCRIPTION

The palladium catalyst employed to initially form the mixture containing 3-pentenoyl chloride, from which 3-pentenoyl chloride is recovered by distillation leaving the still heels containing palladium, may be a mixture of palladium compounds. Suitable palladium compounds include: In General: All zerovalent, divalent, or tetravalent Pd compounds are suitable starting catalysts. The following are Examples:

Palladium halides (PdCl2, PdBr2, PdI2, Na2PdCl4, etc.)
    Palladium sulfate
    Palladium nitrate
    Palladium carboxylates (palladium acetate, etc.)
    Palladium sulfonates
    Organo palladium complexes (palladium acetylacetonate,bis(bibenzylidene acetone) palladium etc.)
    Pyridyl and pyridyl class palladium complexes
    Allylic palladium halides esp crotyl palladium chloride dimer
    Palladium cyanide
    Alkyl and aromatic phosphine complexes of zero and divalent palladium (tetrakis triphenylphosphine palladium, bistriphenylphosphine palladium dichloride, etc.)
    Palladium black
    Supported palladium or its compounds (palladium on alumina, silica, clays, sulfates, carbonates, resins, polymers etc.)
    Palladium oxide The initial reaction conditions for forming the mixture of 3-pentenoyl chloride and palladium catalyst residue from chlorobutenes may be the process described in U.S. Pat. No. 5,288,903.

The drying step which may be carried out between steps f and g, is preferably carried out using a molecular sieve, but other drying methods can also be employed such as the addition of water absorbents, adsorbents and desiccants.

The heels described in the example were obtained as follows:

Two 50 mL continuous stirred tank reactors connected in series were fed with a solution containing 1379.16 gr. of chlorobutene and 3.84 gr. of [Crotyl-Pd-Cl]2 along with CO in a ratio of 0.57 moles CO/mol chlorobutene fed. The temperature of the reactor was 120 C and the CO pressure 2000 psig with a holdup time of 2 hours. The product was collected under an atmosphere of CO. The solution containing the 3-pentenoylchloride, chlorobutene and catalyst were distilled under reduced pressure to take chlorobutene and part of the 3-pentenoylchloride overhead. The heels of the distillation were diluted with chlorobutene to same volume as initial charge and this feed fed through reactor again at the same conditions. This cycle was repeated 13 times. The following chart gives the conditions for each cycle along with the amounts of 3-pentenoylchloride produced each cycle.

| Cycle # | Dist. Press. (mm Hg) | Final PotTemp (C.) | gr 3PACl fed to still | gr 3PACL overhead |
| --- | --- | --- | --- | --- |
| 1 | 200 | 85 | 397.2 | 166.0 |
| 2 | 200 | 92 | 483.6 | 258.4 |
| 3 | 200 | 108 | 502.4 | 465.4 |
| 4 | 200 | 139 | 412.0 | 312.8 |
| 5 | 500 | 119 | 407.2 | 95.2 |
| 6 | 750 | 122 | 531.7 | 119.8 |
| 7 | 200 | 118 | 601.7 | 521.8 |
| 8 | 150 | 114 | 405.3 | 363.0 |
| 9 | 150 | 114 | 394.3 | 367.6 |
| 10 | 150 | 104 | 276.4 | 237.8 |
| 11 | 150 | 122 | 272.2 | 246.2 |
| 12 | 150 | 117 | 336.7 | 294.0 |
| 13 | 150 | 125 | 351.5 | 331.0 |

After the 13th cycle 55.7 gr of the heels were treated as described in Example 1.

EXAMPLE 1:

55.7 g of distillation heels ([Pd]=5779 ppm) were combined with 8 mL of water and 100 mL of HCl (37%) and heated at 105° C. for 2.5 hours. After cooling at 25° C., 100 mL of chlorobutenes was added. The organic phase was separated from the HCl phase (105 g). The concentration of palladium in the HCl phase was 2139 ppm.

The organic phase was concentrated via rotatory evaporation at 25° C. and then combined with 100 mL of HCl (37%) and heated at 105° C. for 2 hours. After cooling the mixture to 25° C., 100 mL of chlorobutenes was added. The organic phase was separated from the HCl phase (103 g). The concentration of palladium in the HCl phase was 302 ppm.

The organic phase was concentrated via rotatory evaporation at 25° C. and then combined with 100 mL of HCl (37%) and heated at 105° C. for 2 hours. After cooling the mixture to 25° C., 100 mL of chlorobutenes was added. The organic phase was separated from the HCl phase (94.8 g). The concentration of palladium in the HCl phase was 67 ppm.

The HCl solutions obtained from above were combined with 500 mL of chlorobutenes in a 2L round bottom flask equipped with a Dean Stark apparatus. A sparge tube was introduced into the liquid to maintain a carbon monoxide atmosphere during the distillation. A two phase distillate (chlorobutenes and HCl conc.) was collected at 72° C. After collecting 270 g of HCl, the distillation was stopped. The chlorobutene solution was cooled to 25° C. and dried over 10 g of Molecular Sieves 4A.

60 g of chlorobutene solution, containing the catalyst, was loaded into a 100 mL autoclave and heated at 25° C. under carbon monoxide (850 psig total pressure) for 3 hours. GC analysis indicated the formation of 3-pentenoyl chloride and the conversion of chlorobutenes to 3-pentenoyl chloride was 18.8 mole %.

What is claimed is:

1. A process for the preparation of 3-pentenoyl chloride which comprises (a) treating the still heels obtained by the distillation of 3-pentenoyl chloride from a reaction mixture containing palladium catalyst residue with concentrated hydrochloric acid at a temperature in the range of 100 to 120 degrees C., (b) combining the product of step a with chlorobutene, (c) allowing the product of step b to form two phases, an organic phase, and a hydrochloric acid phase containing palladium catalyst residue, (d) separating the two phases of step c, (e) combining the hydrochloric acid phase obtained in step d with chlorobutene (f) distilling under a carbon monoxide atmosphere at a temperature of about 70 to 75 degrees C. the product of step e, an azeotropic mixture, until only one phase is observed, namely a phase containing chlorobutene and simultaneously formed crotyl palladium chloride, (g) heating the product of step f containing chlorobutene and crotyl palladium chloride at a temperature in the range of about 90 to 190 degrees C. under a carbon monoxide pressure of about 250 to 5,000 pounds per square inch, and (h) recovering 3-pentenoyl chloride from the product of step g by distillation.

2. The process of claim 1 in which still heels remain after step (i), and the still heels are recycled to step (a).

3. The process of claim 1 in which the product of step f is dryed before the product is treated in accordance with step g.

* * * * *